US005779596A

United States Patent [19]

Weber

[11] Patent Number: 5,779,596
[45] Date of Patent: Jul. 14, 1998

[54] REMOTE CONTROLLER MECHANISM FOR USE WITH A VIDEOCASSETTE RECORDER OR THE LIKE

[76] Inventor: Daniel W. Weber, 7791 Old State Rd., Cranesville, Pa. 16410

[21] Appl. No.: 754,756

[22] Filed: Nov. 21, 1996

Related U.S. Application Data

[63] Continuation-in-part of Ser. No. 531,319, Sep. 20, 1995, abandoned.

[51] Int. Cl.$^6$ ...................................................... A61B 5/04
[52] U.S. Cl. ................................. 482/4; 482/6; 482/57; 482/902
[58] Field of Search .................... 482/1-9, 54, 900-902, 482/57, 51

[56] References Cited

U.S. PATENT DOCUMENTS

| 5,120,228 | 6/1992 | Stahl et al. | 434/258 |
| 5,527,239 | 6/1996 | Abbondanza | 482/901 |

Primary Examiner—Richard J. Apley
Assistant Examiner—Glenn Richman

[57] ABSTRACT

A remote controller mechanism for use with a piece of exercise equipment such as an exercise bicycle or apparatus and a remotely controllable electronic device wherein the piece of exercise equipment has an electronic sensor that outputs a train of electronic pulses as a function of the speed at which the piece of exercise equipment is operated and wherein the remotely controllable electronic device has a first and a second operational mode, the remote controller mechanism including an interface mechanism for receiving the train of electronic pulses; a speed determination mechanism coupled to the interface mechanism for receiving the train of electronic pulses and then determining a present speed based upon the train of electronic pulses; a speed selection mechanism for allowing a desired minimum speed to be set by the user; a comparator mechanism coupled to the speed determination mechanism and the speed selection mechanism for comparing the present speed to the minimum speed and then outputing a result of the comparison; and a remote control mechanism coupled to the comparator mechanism for generating a first signal for placing the remotely controllable device in its first operational mode when the present speed is greater than the minimum speed and for generating a second signal for placing the remotely controllable device in its second operational mode when the present speed is less than the minimum speed.

7 Claims, 9 Drawing Sheets

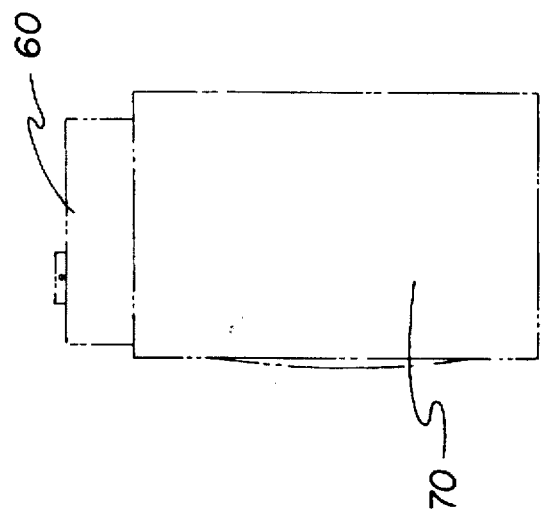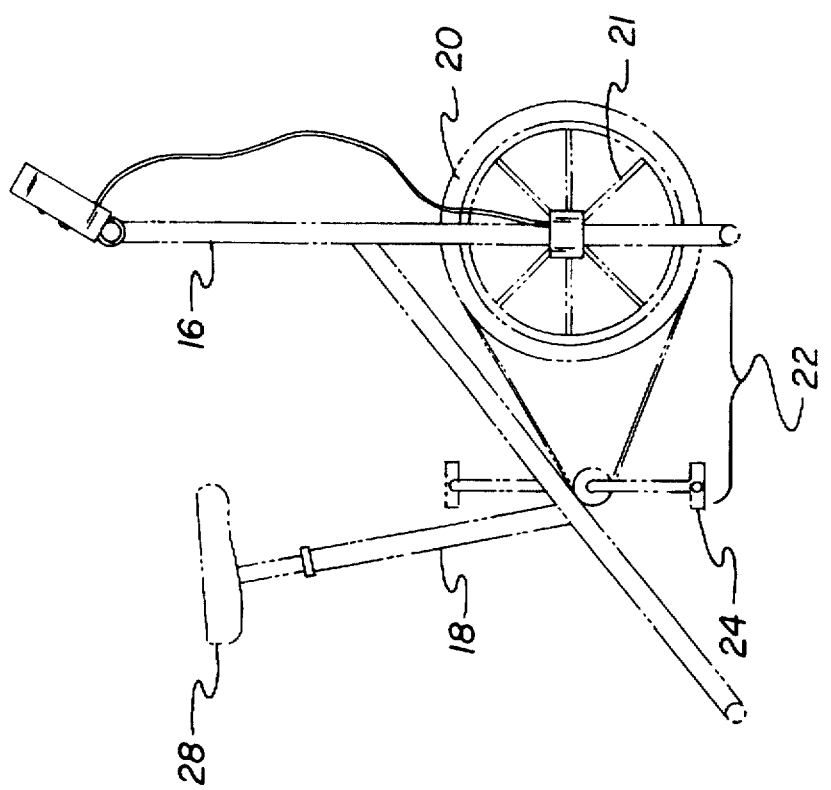
FIG. 2

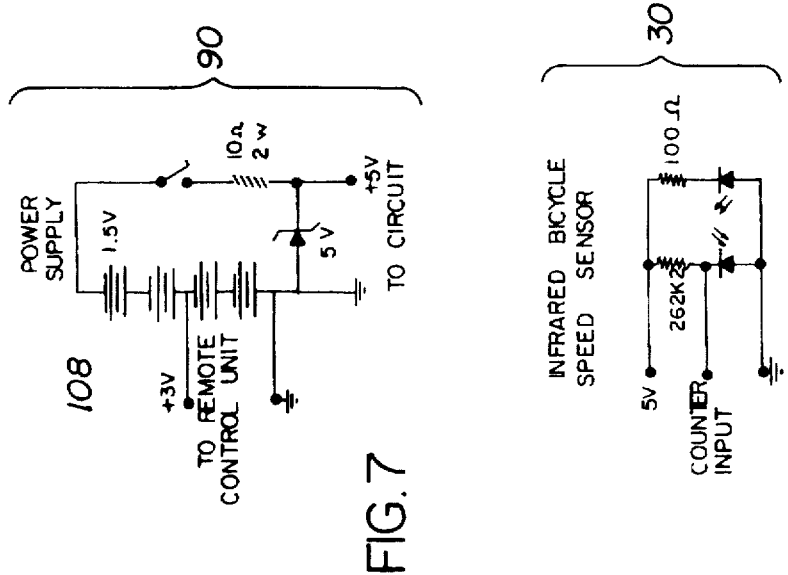
FIG. 7
FIG. 8
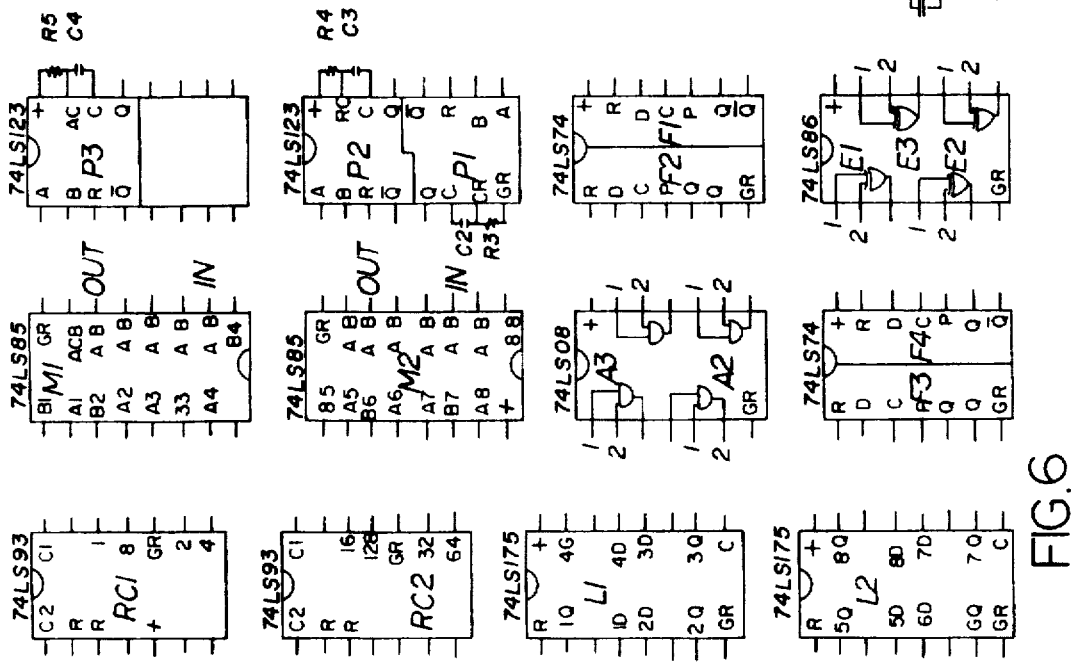
FIG. 6

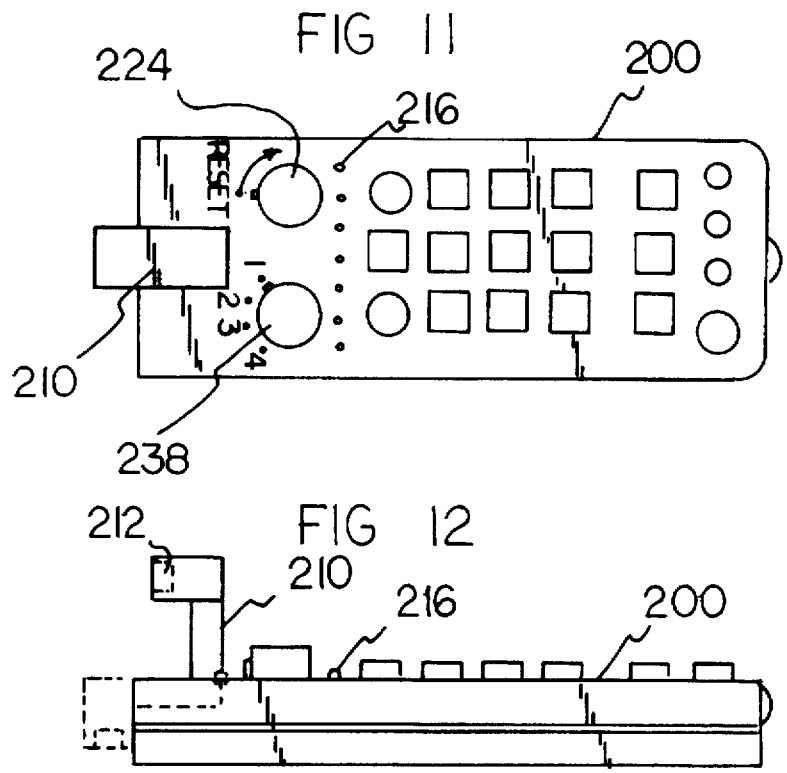
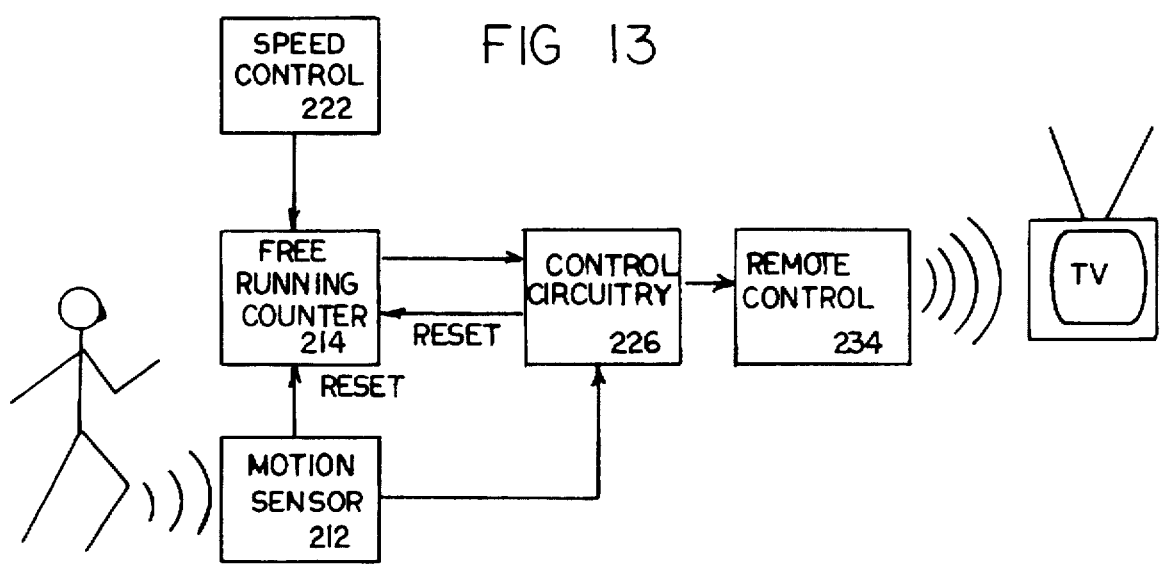

ns
5,779,596

REMOTE CONTROLLER MECHANISM FOR USE WITH A VIDEOCASSETTE RECORDER OR THE LIKE

BACKGROUND OF THE INVENTION

1. Background Information

This application is a continuation-in-part application of an application filed Sep. 25, 1995 under Ser. No. 08/531,319 abandoned Nov. 26, 1996.

2. Field of the Invention

The present invention relates to a remote controller mechanism for use with a videocassette recorder (VCR), television (TV) or the like and more particularly pertains to remotely controlling a television, VCR or the like as a function of an exercise being performed.

3. Description of the Prior Art

The use of electronic remote control mechanisms is known in the prior art. More specifically, electronic remote control mechanisms heretofore devised and utilized for the purpose of controlling the operations of an electronic device such as a videocassette recorder are known to consist basically of familiar, expected and obvious structural configurations, notwithstanding the myriad of designs encompassed by the crowded prior art which have been developed for the fulfillment of countless objectives and requirements.

By way of example, U.S. Pat. No. 4,512,567 to Phillips discloses an exercise bicycle apparatus particularly adapted for controlling video games. U.S. Pat. No. 4,613,129 to Schroeder et al. discloses an exercise bicycle attachment. U.S. Pat. No. 4,938,475 to Sargeant et al. discloses a bicycle racing training apparatus. U.S. Pat. No. 5,202,627 to Sale discloses a pedaling monitor for displaying instantaneous pedal velocity and position. U.S. Pat. No. 5,240,417 to Smithson et al. discloses a system and method for bicycle riding simulation.

In this respect, the remote controller mechanism for use with an exercise bicycle/apparatus and a videocassette recorder or the like according to the present invention substantially departs from the conventional concepts and designs of the prior art, and in doing so provides an apparatus primarily developed for the purpose of remotely controlling a television, VCR or the like as a function of an exercise being performed.

Therefore, it can be appreciated that there exists a continuing need for new and improved exercise remote controller mechanism for use with a television or the like which can be used for remotely controlling a television, VCR or the like as a function of an exercise being performed. In this regard, the present invention substantially fulfills this need.

SUMMARY OF THE INVENTION

In the view of the foregoing disadvantages inherent in the known types of electronic remote control mechanisms now present in the prior art, the present invention provides an improved remote controller mechanism for use with an exercise bicycle/apparatus and a videocassette recorder or the like. As such, the general purpose of the present invention, which will be described subsequently in greater detail, is to provide a new and improved remote controller mechanism for use with an exercise bicycle/apparatus and a videocassette recorder or the like and method which has all the advantages of the prior art and none of the disadvantages.

To attain this, the present invention essentially comprises, in combination, a stationary exercise bicycle having a rotatable flywheel and a pedaling mechanism operable therewith for allowing a user to rotate the flywheel at various speeds while pedaling. An electronic sensor means is included coupled to the exercise bicycle for generating a train of electronic pulses wherein a time interval between consecutive pulses of the pulse train is a function of the speed of the rotating flywheel of the exercise bicycle. An electronic speed determination means is included and coupled to the exercise bicycle for determining a present speed of the flywheel of the exercise bicycle by counting pulses of the pulse train that are received within a given period of time. An electronic interface means is included coupled to the exercise bicycle for allowing the speed determination means to be removably coupled to the sensor means. An electronic speed selection means is included and coupled to the exercise bicycle for allowing the pedaling user to manually set a desired minimum speed. An electronic comparator means is included and coupled to the exercise bicycle, the speed determination means, and the speed selection means for comparing the present speed to the minimum speed and then outputting a result of the comparison. A videocassette recorder is provided for playing a videocassette and is positionable at a location remote from the exercise bicycle. The videocassette recorder has a playback function that is activated through receipt of a remote first infrared signal and a pause function that is activated through receipt of a remote second infrared signal. A television is provided and coupled to the videocassette recorder. The television is responsive to the videocassette recorder for displaying video that is stored on videocassette to the user of the exercise bicycle when the playback function of the videocassette recorder is activated and for pausing such video when the pause function of the videocassette recorder is activated. Lastly, a remote control means is included and coupled to the exercise bicycle. The remote control means is used for generating a first infrared signal for activating the playback function of the videocassette recorder when the present speed is greater than the minimum speed and is also used for generating a second infrared signal for activating the pause function of the videocassette recorder when the present speed is less than the minimum speed.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved remote controller mechanism for use with an exercise bicycle/apparatus and a videocassette recorder or the like which has all the advantages of the prior art electronic remote control mechanisms and none of the disadvantages.

It is another object of the present invention to provide a new and improved remote controller mechanism for use with an exercise bicycle/apparatus and a videocassette recorder or the like which may be easily and efficiently manufactured and marketed.

It is a further object of the present invention to provide a new and improved remote controller mechanism for use with an exercise bicycle/apparatus and a videocassette recorder or the like which is of durable and reliable construction.

An even further object of the present invention is to provide a new and improved remote controller mechanism for use with an exercise bicycle/apparatus and a videocassette recorder or the like which is susceptible of a low cost of manufacture with regard to both materials and labor, and which accordingly is then susceptible of low prices of sale to the consuming public, thereby making such a remote controller mechanism for use with an exercise bicycle/apparatus and a videocassette recorder or the like economically available to the buying public.

Still yet another object of the present invention is to provide a new and improved remote controller mechanism for use with an exercise bicycle/apparatus and a videocassette recorder or the like which provides in the apparatuses and methods of the prior art some of the advantages thereof, while simultaneously overcoming some of the disadvantages normally associated therewith.

Even still another object of the present invention is to remotely control a television, VCR or the like as a function of an exercise being performed.

Lastly, it is an object of the present invention to provide a new and improved remote controller mechanism for use with an exercise bicycle/apparatus and a videocassette recorder or the like comprising interface means for receiving the train of electronic pulses; speed determination means coupled to the interface means for receiving the train of electronic pulses and then determining a present speed based upon the train of electronic pulses; speed selection means for allowing a desired minimum speed to be set by the user; comparator means coupled to the speed determination means and the speed selection means for comparing the present speed to the minimum speed and then outputting a result of the comparison; and remote control means coupled to the comparator means for generating a first signal for placing the remotely controllable device in its first operational mode when the present speed is greater than the minimum speed and for generating a second signal for placing the remotely controllable device in its second operational mode when the present speed is less than the minimum speed.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 2 is a side-elevational view of the preferred embodiment of the present invention.

FIG. 6 is an integrated circuit layout for the present invention.

FIG. 7 is a schematic diagram of the power supply of the present invention.

FIG. 8 is a schematic diagram of the infrared speed sensor for monitoring bicycle speed of the present invention.

FIG. 10 is an enlarged view of the interface of the sensor mechanism with the vanes on the flywheel of the exercise bicycle for use in attaining a speed measurement.

FIG. 11 is a top view of the remote control mechanism of an alternate embodiment of the present invention.

FIG. 12 is a side view of the remote control mechanism of the alternate embodiment of the present invention.

FIG. 13 is a block diagram generally depicting the electrical components of the alternate embodiment of the present invention.

The same reference numerals refer to the same parts through the various Figures.

DESCRIPTION OF THE PREFERRED EMBODIMENT

Figure 1:
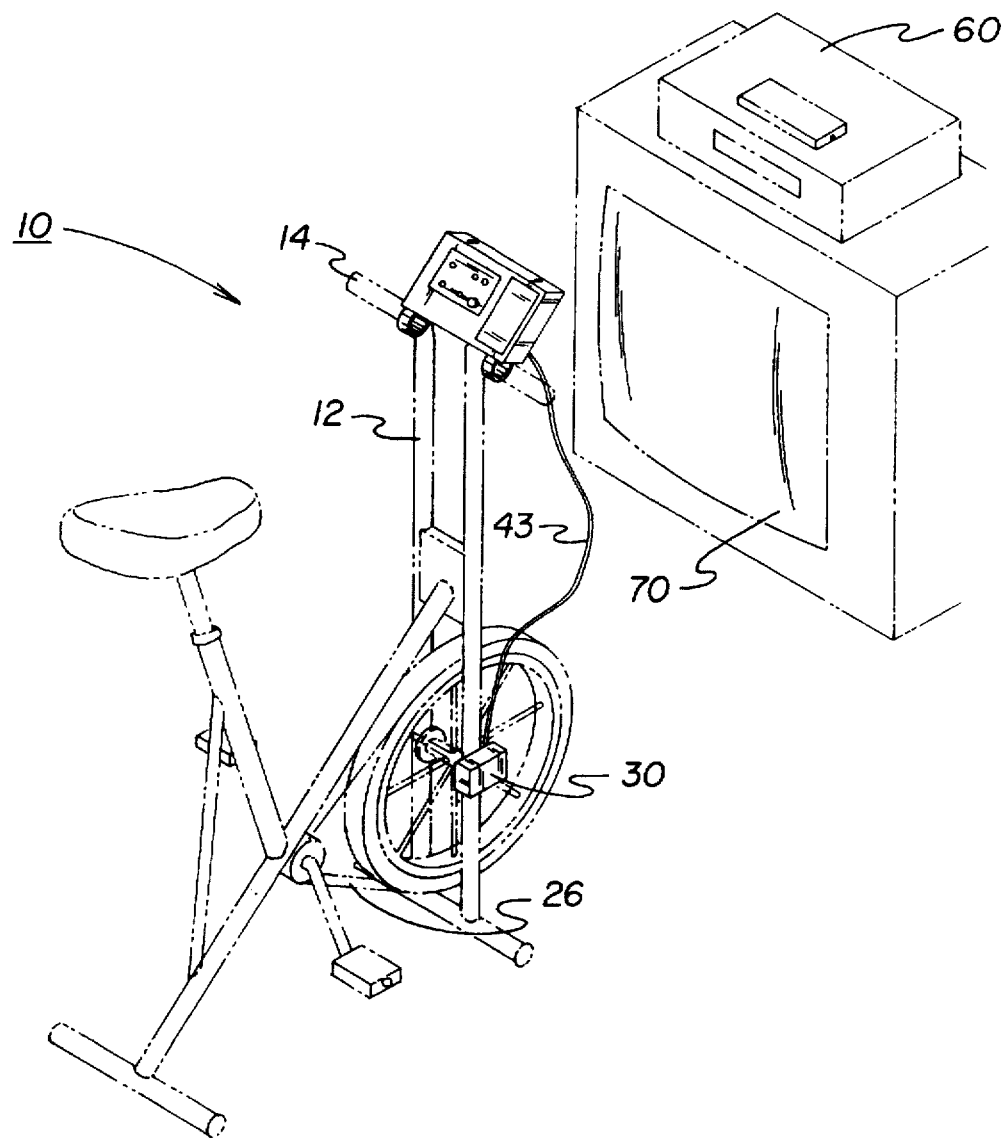
FIG. 1 is a perspective view of the preferred embodiment constructed in accordance with the principles of the present invention.
Figure 4:
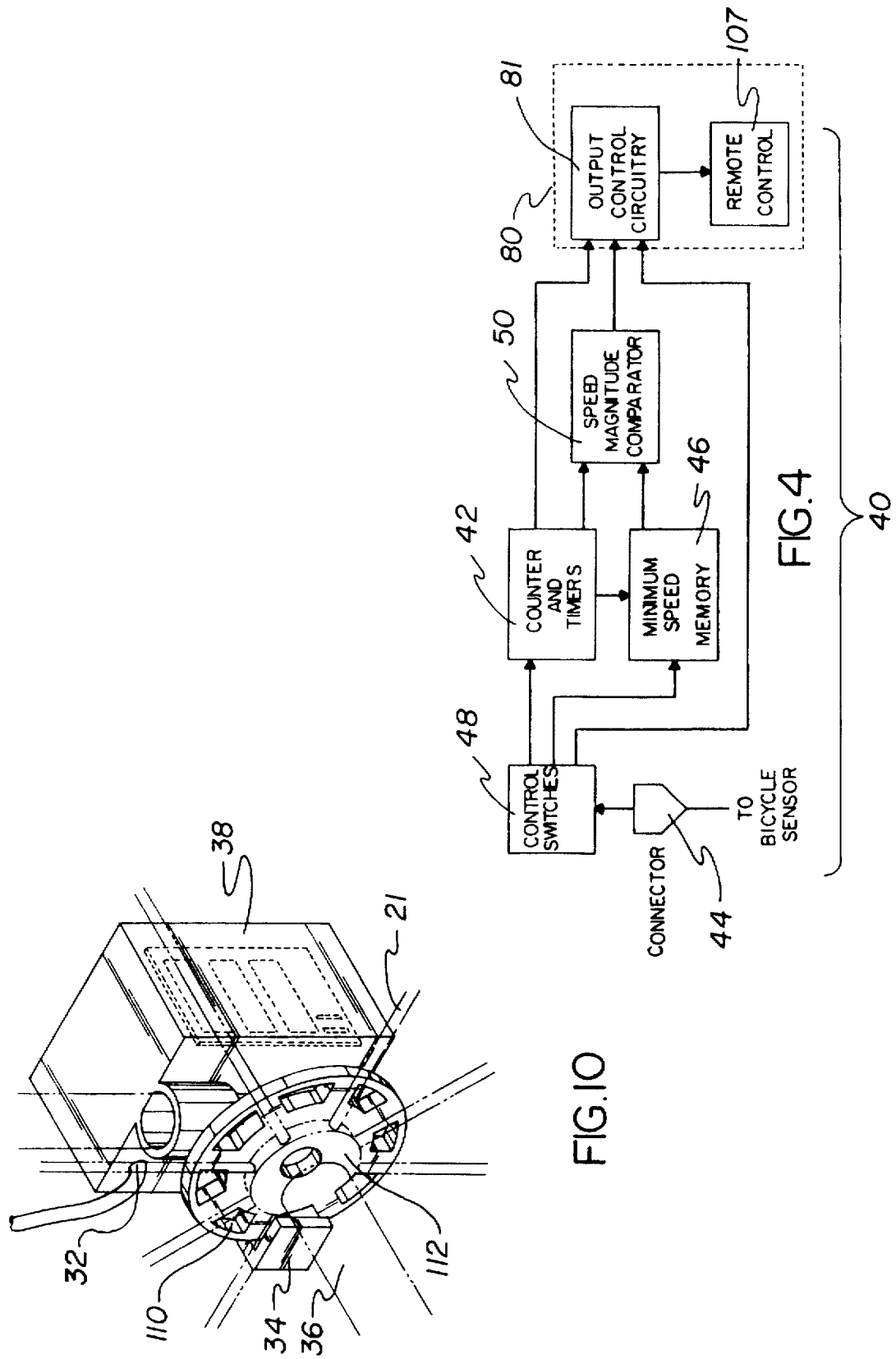
FIG. 4 is a top level block diagram of the present invention.
Figure 5:
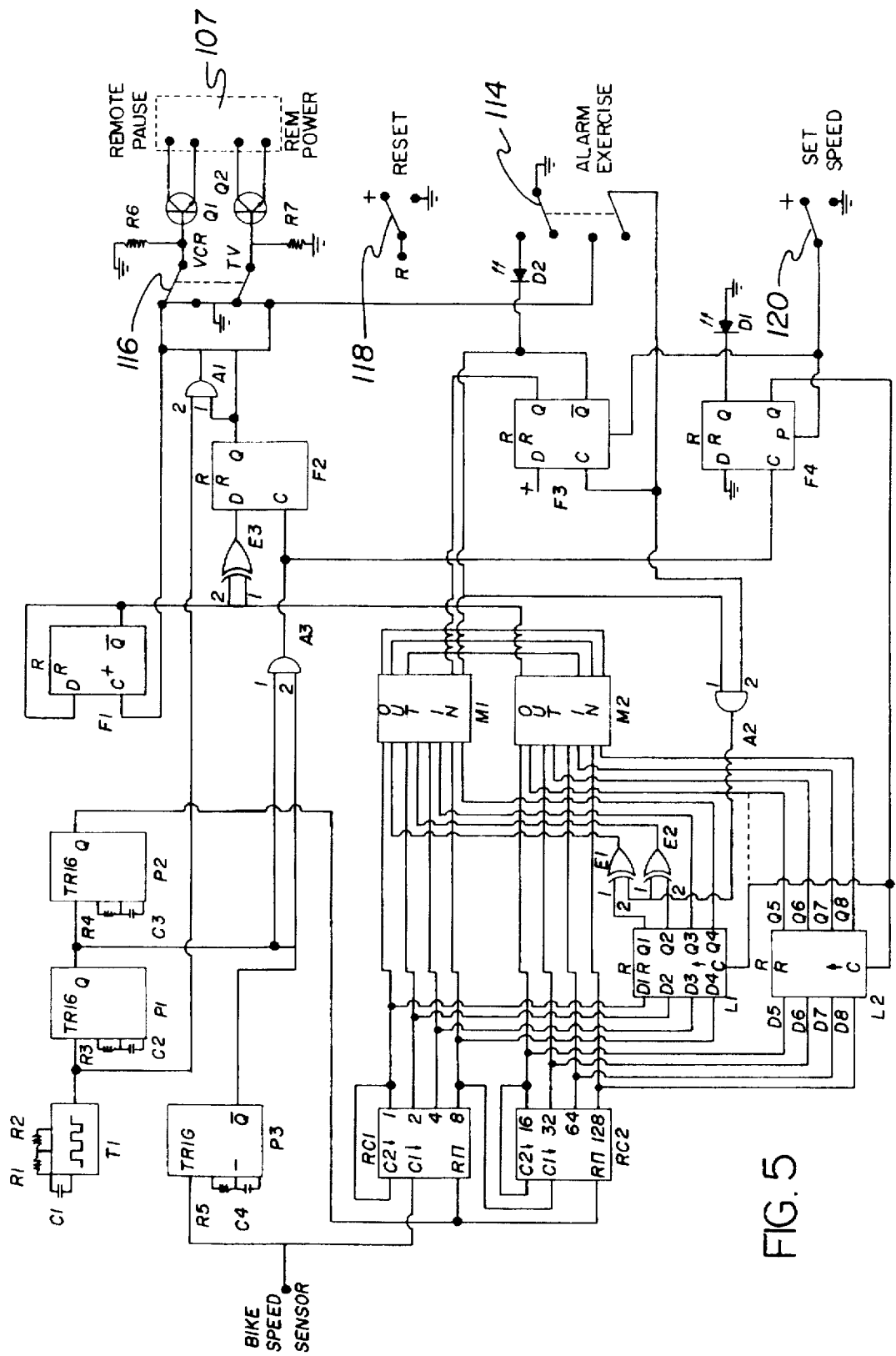
FIG. 5 is a schematic diagram of the present invention.

With reference now to the drawings, and in particular, to FIGS. 1, 4 and 5 thereof, the preferred embodiment of the new and improved remote controller mechanism embodying the principles and concepts of the present invention and generally designated by the reference number 10 will be described.

The preferred embodiment of the present invention comprises a plurality of components. In their broadest context, such components include a piece of exercise equipment such as a bicycle, an electric circuit, and a remotely controllable electronic device. Such components are individually configured and correlated with respect to each other to provide a way to control an electronic device such as a videocassette recorder, television receiver, or similar piece of electronic equipment through the use of a piece of exercise equipment.

Specifically, the present invention includes a stationary exercise bicycle 12. Bicycle 12 has a handle bar assembly 14 to which a yoke 16 is extended downward. Frame 18 is coupled to yoke 16. Yoke 16 also holds a rotatable flywheel 20 with spokes 21. The flywheel is actuated through a pedaling mechanism 22 formed of pedals 24 and drive belt 26. The pedaling mechanism is operable by a user for rotating the flywheel at various speeds while pedaling. The user can rest upon an adjustable seat 28. A bicycle such as the Sears® XC1000 can be utilized.

An electronic sensor mechanism 30 formed of an infrared emitter 32 and detector 34 is also provided. The sensor mechanism 30 is coupled to the exercise bicycle near the axle 36 of the flywheel. The emitter 32 and detector 34 are contained in a rigid housing 38. The sensor mechanism is used for generating a train of electronic pulses wherein a time interval between consecutive pulses of the pulse train is a function of the speed of the rotating flywheel 20 of the exercise bicycle 12. Thus, the faster the user pedals, the faster the speed of the flywheel, and the closer in time the electronic pulses of the pulse train are to each other.

An electric circuit 40 as shown in FIG. 4 is also provided. The circuit includes an electronic speed determination mechanism 42 that is formed of a plurality of timers and counters. The speed determination mechanism is coupled to the exercise bicycle 12 and is used for determining a present speed of the flywheel 20. The speed determination mechanism accomplishes this by counting pulses of the pulse train that are received within a given period of time.

Also provided as part of the circuit is an electronic interface mechanism 44. The mechanism is formed of a conventional connector jack 106 and electronic cable 43. The interface mechanism is coupled to the exercise bicycle 20 and allows the electric circuit 40 and speed determination means 42 to be removably coupled to the sensor mechanism 30.

In addition, an electronic speed selection mechanism 46 is coupled to the exercise bicycle 12. The speed selection mechanism allows the pedaling user to manually set and store a desired minimum speed. As shown in FIG. 4, control switches 48 are an integral part of both the speed determination mechanism 42 and the speed selection mechanism 46.

Coupled to the exercise bicycle, the speed determination mechanism 42, and the speed selection mechanism 46 is an electronic comparator mechanism 50. The electronic comparator mechanism is used for comparing the present speed to the minimum speed as set by the user and then outputting a result of the comparison.

The aforementioned components are used in conjunction with a videocassette recorder 60. The videocassette recorder is used for playing standard videocassettes and is positionable at a location remote from the exercise bicycle and electric circuit 40. The videocassettes are positionable for play through door 62 of the videocassette recorder. The videocassette recorder has a playback function that is activated through receipt of a remote first infrared signal that is received by an integral infrared detector 64. In addition, the videocassette recorder has a pause function that is activated through receipt of a remote second infrared signal.

A television 70 is coupled to the videocassette recorder 60 with a cable 71. The television is responsive to the videocassette recorder during its playback function for displaying video upon its screen 72. The video that is displayed is a function of information stored on a removable videocassette. The video on the television is paused when the pause function of the videocassette recorder is activated.

Activation of video and subsequent pausing thereof is accomplished through a remote control mechanism 80 that is part of the electric circuit 40. The remote control mechanism is formed of output control circuitry 81 and is coupled to the exercise bicycle 12 and the comparator mechanism 50 as well as the counters and timers 42. The remote control mechanism is used for generating and radiating a first infrared signal 82 into free space for activating the playback function of the videocassette recorder 60. This first infrared signal is radiated when the present speed of the exercise bicycle is greater than the minimum speed set by the user. The remote control mechanism is also used for generating and radiating a second infrared signal into free space for activating the pause function of the videocassette recorder. This second infrared signal is radiated when the present speed of the exercise bicycle is less than the minimum speed set by the user.

In addition, the electric circuit 40 includes a power supply mechanism 90. The power supply mechanism is coupled to the electric circuit and sensor mechanism 30 and provides power for their operation. Either battery or conventional line power can be employed. Preferably, battery power is used.

The present invention provides a way to automatically operate a VCR/TV remote controlled unit. In other words it is a control controller. The present invention has two basic functions. The first function allows the present invention to operate as a motivational aide for exercising. The second function allows the present invention to operate as an alarm. The physical layout of the present invention contains a control box 100 with various switches 102, indicator lights 104, and a modular phone jack 106 input plug. Input is received from an external sensor 30. The present invention includes a circuit board containing timers, pulse counters, memory latches, magnitude comparators, control gates and other circuit elements. This circuit board then connects to a conventional VCR/TV remote control unit 107 that is utilized as part of the remote control mechanism 80. The present invention is powered by four C-size batteries 108.

An integral or external sensor 30 is required for the present invention to operate. The sensor sends voltage pulses to the present invention in relation to the speed of the bicycle 12 or other monitored apparatus. The voltage pulses must be discrete, single pulses. The sensor 30 is not necessarily a required part of the invention. There are commercially available optical or magnetic sensor devices on the market which are suitable and employable for this type of application such as "cruise control" speed sensors used on cars, for example.

An infrared speed sensor assembly formed of a detector 32 and emitter 34 can be utilized and attached to the exercise bicycle. When using the infrared sensor, eight metal tabs 110 are attached to the bicycle wheel. Preferably, the tabs are attached to the bicycle's speedometer 112 that is mounted near the hub or axle of its flywheel. The tabs are located between the infrared emitter and detector of the speed sensor assembly as the bicycle is pedaled. The sensor assembly is attached with screws to a support rod having 7/64" holes drilled in it. The tabs are evenly spaced and opaque to infrared light. The remaining portion of present invention can then be mounted to the bicycle handle bar assembly 14.

The present invention may operate as an exercise aide or an alarm. When used as a motivational aide for exercising, the present invention causes a VCR 60 to respond to the operation of an exercise bicycle. A videotape is placed in the VCR, threaded up by playing it, and put in pause mode. The present invention is turned on. When the bicycle is pedaled, the present invention senses the motion and activates the pause function of the remote control unit. This allows the video tape to start playing. When the bicycle is stopped, the present invention again senses the lack of motion and again activates the remote control unit thereby stopping the tape. This is the basic operation of the present invention. If so desired while pedaling the bicycle, the present speed of the bicycle may be stored in memory as a minimum speed at which to play back the video tape. In this case the VCR is put in pause mode if the speed of the bicycle falls below the stored minimum speed. The VCR will be put in play mode when the speed of the bicycle is equal to or greater than the stored minimum speed. By adding a switch to the output, a TV 70 set may be controlled by the present invention in place of the VCR. In this case instead of the VCR being put in pause mode, the TV set would be turned off. Instead of the VCR being put into play mode, the TV set would be turned on. This allows the viewing of something other than a video tape while exercising such as broadcast, cable, or satellite programming.

Figure 3:
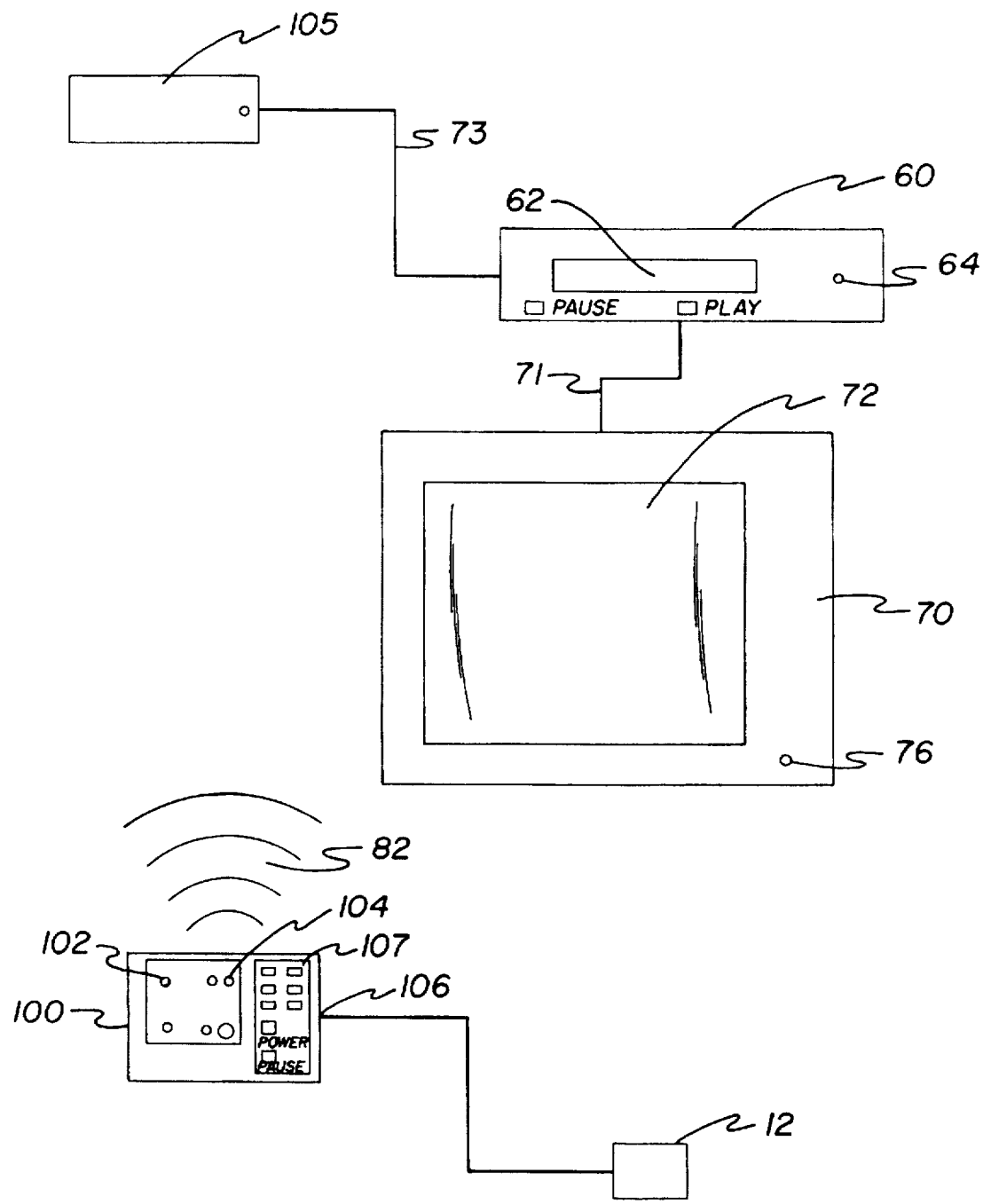
FIG. 3 depicts the operation of the remote control mechanism with a videocassette recorder connected with a television as well as an ancillary piece of electronic equipment that can also be remotely controlled via the remote control mechanism.

Besides using the bicycle, any exercise machine or equivalent that can be fitted with a sensor which provides voltage pulses can be used as input to the present invention through the modular phone jack. These include but are not limited to treadmills, stair steppers, ski machines, and rowing machines. In addition, any electronic device 105 which can be controlled by a remote control unit can be controlled by the present invention (for example, as shown in FIG. 3, wherein the device 105 is connected to the switched or unswitched power receptacle of videocassette recorder 60 though power cable 73). These include but are not limited to laser disc players both video and audio, cassette players, radio receivers, cable TV boxes, satellite receivers and even room lights. If so desired, multiple inputs and output remote control units could be connected to the same present invention with switches to select the desired input and output.

The present invention can also operate as alarm. Some examples are:

(1) You have clothes in a clothes dryer that need to be taken out at the end of the cycle to prevent wrinkling. You are in a room where hearing the dryer buzzer-is difficult or it is noisy or you are hard-of-hearing. You are watching TV. When the clothes are done, the TV turns off. If the TV was off, it will turn on.

(2) Someone rings the door bell but you have difficulty hearing it. You are watching TV. When the door bell rings, the TV turns off.

(3) You are baking a cake and are in a room where it is difficult to hear the oven signal telling you to take the cake out of the oven. You are watching TV. When the oven alarm buzzes, the TV turns off.

In fact, any device that can provide a voltage pulse to the present invention through the phone jack 106 can activate the system. These include but are not limited to a smoke detector, telephone, alarm clock, computer, or home security system. Likewise, devices other than a TV may be controlled. When the present invention is in alarm mode and ready to react to an alarm signal, an indicator lights to let you know if you remembered to set it. The light turns off when the alarm is triggered. When the present invention is used in this mode it would be desirable to use an alternate AC power source. An AC power supply may be easily added to the present invention. A common 6 volt DC adapter could be plugged into an AC outlet and fed into a jack in the control box. If AC power is used exclusively and no batteries are installed, then two batteries must be inserted into the remote control unit.

The system will be described with the alarm/exercise switch 114 in the exercise mode or closed position. The circuit operation in alarm mode will be described in the last section. Since an eight bit counting system is used, the counter, memory latches, and magnitude comparator consist of two four-bit components each. They will be referred to as RC1/RC2, L1/L2, and M1/M2 respectively as per circuit diagram of FIG. 5.

The present invention must determine the present speed of the bicycle. This is done by a common method of counting pulses in a given time interval. Referring to FIGS. 5 and 6, the circuit components involved are T1, P1, P2, and RC1/RC2. The counter, RC1/RC2, is clocked by tabs on the bicycle wheel which interrupt a beam generated by an infrared sensor circuit. The faster the bicycle is pedaled, the higher the counter output is for the given time interval. By increasing the number of tabs on the bicycle wheel, more accurate speed sensing is possible. The present invention could handle 64 tabs with the bicycle being pedaled at 38 miles-per-hour. Eight tabs work effectively and are easy to space evenly. T1 is the system clock which provides the timing interval of approximately 0.67 second (see FIG. 9). P1 is a monostable multivibrator or pulse generator which is triggered by T1 at the end of the time interval. The pulse from P1 clocks other circuit components (which will be described later) which capture data based on the output of the counter, RC1/RC2, at that time. This method of data capture eliminates the need for a memory register to actually store the present output of the counter. At this point, the counter output will be referred to as the "present speed". The negative-going edge of the pulse from P1 then triggers pulse generator P2. The pulse from P2 resets the counter, RC1/RC2, to zero.

Another function of the circuit is to store a "present speed" in memory to act as a minimum speed at which the bicycle activates the remote control unit. If no speed is stored in memory, the memory output is zero. The circuit components involved are RC1/RC2, L1/L2, F4, and D1. Since there is no "present speed" memory register, the counter output from RC1/RC2 must be stored in memory latches, L1/L2, on the output pulse of P1 which defines the "present speed". This is accomplished by flip-flop F4. When the set-speed button 120 is pressed while the bicycle is going at the desired speed, the output of F4 is set to a high level. The next output pulse from P1 then clocks the output of F4 back to a low level. This causes the complimentary output of F4 to switch from a low level to a high level, which clocks memory latches L1/L2. This stores the output of RC1/RC2 in memory. This memory speed will be referred to as the "minimum speed". LED D1 connected to the output of F4, lights when the set-speed button is pressed and turns off when the "minimum speed" has been stored by the pulse from P1.

The next function of the circuit is to compare the "present speed" with the "minimum speed" to determine if the "present speed" is less than the "minimum speed". The circuit components involved are RC1/RC2, L1/L2, and M1/M2. The magnitude comparator, M1/M2, is constantly comparing the "minimum speed" in L1/L2 to the output of RC1/RC2. The output of M1/M2 is sent to other circuit components, described later, whose output is captured by a pulse from P1. Therefore the output of M1/M2 is only sampled when the output of RC1/RC2 becomes the "present speed" on a pulse from P1. It is best to set "minimum speed" at several miles per hour less than your cruising speed. This avoids constantly starting and pausing the VCR by hovering back and forth across the minimum speed threshold.

In order for the present invention to know if it must activate the remote control unit, it must know two things: the present mode of the VCR, playing or paused, and whether the "present speed" is less than the "minimum speed" or not. The circuit components involved are F1, M1/M2, E3, F2, P1, A1, T1, Q1, and Q2. The mode of the VCR is stored in flip-flop F1. Each time the remote control unit is activated, F1 is toggled to reflect the new mode of the VCR. The F1 complimentary output is used and is high when the VCR is paused and low when the VCR is playing. M1/M2 supplies the "present speed" /"minimum speed" comparison result as described earlier. The output of M1/M2 is high if the "present speed" is less than the "minimum speed" and low if the "present speed" is greater than or equal to the "minimum speed".

These two pieces of information are sent to exclusive-or-gate E3. If both inputs are the same, it means the VCR is in the proper mode and the remote control unit does not need to be activated. Accordingly, the output of E3 is low. If the inputs are different, the mode of the VCR must be changed and the output of E3 is high. When the output of E3 is high at the time its output is stored in flip-flop F2 by a pulse from P1, and-gate A1 is enabled. This allows the next high output pulse from system clock T1 to turn on transistor Q1 thereby activating the pause function of the remote control unit. This also toggles F1 to reflect the new mode of the VCR as described earlier.

The output of A1 can be sent to transistor Q2 instead of Q1 by a VCR/TV switch 116. Q2 then activates the "TV power" function of the remote control unit instead of the VCR "pause" function. The mode of the remote control unit itself does not need to be changed. If left in "TV mode" the VCR transport functions will still operate.

Figure 9:
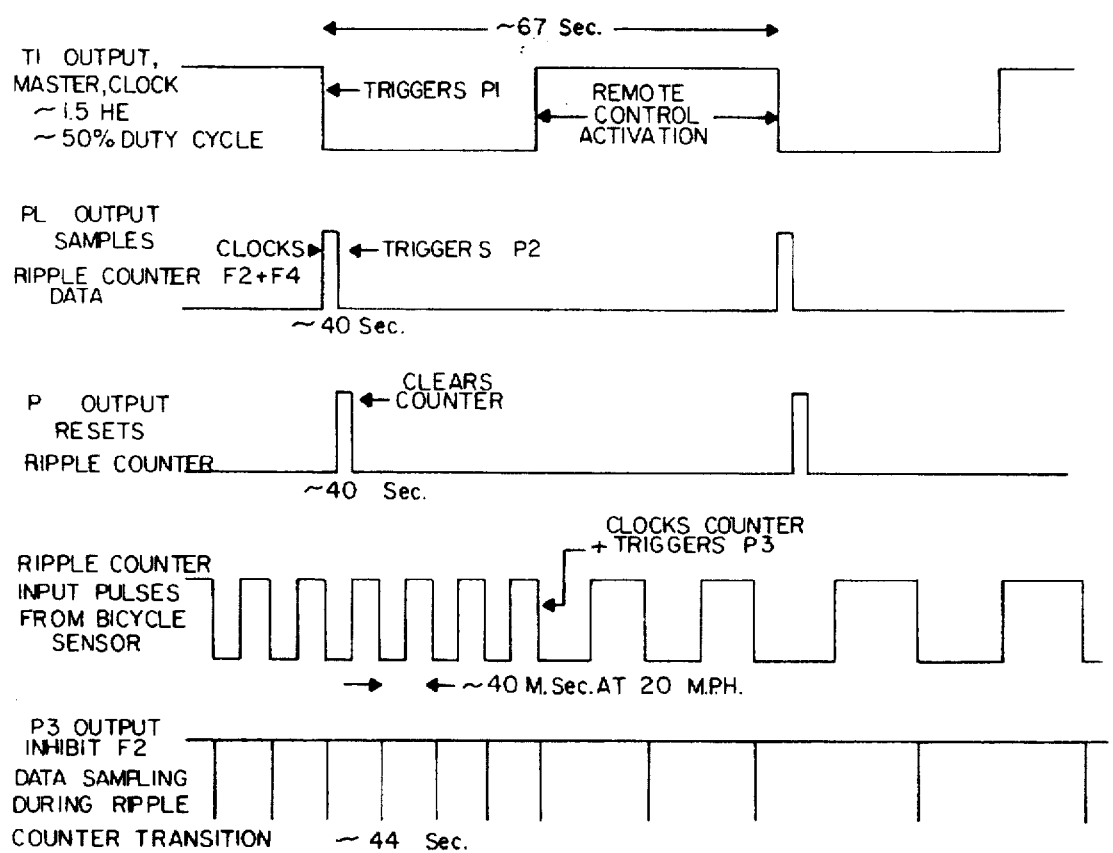
FIG. 9 is a timing diagram for the present invention.

RC1/RC2 is a ripple counter which means each bit is clocked sequentially not synchronously. It takes approximately 100 nanoseconds to transition from one count to the next. If data is sampled when P1 clocks F2 while RC1/RC2 is in transition, an erroneous result may occur. To prevent this, circuit components P3 and A3 have been included. When a clock pulse arrives at RC1/RC2 from the bicycle sensor, pulse-generator P3 is also triggered. The complimentary output of P3 provides a short negative pulse which momentarily inhibits and-gate A3. This prevents the longer pulse from P1 from clocking F2 until RC1/RC2 have stabilized as shown in FIG. 9.

If no speed has been set in memory, the "minimum speed" is zero. This means that the bicycle has no control over the VCR since the "present speed" will always be greater than or equal to the "minimum speed" of zero. To allow the bicycle to control the VCR when no minimum speed is set, circuit components A2, F3, E1, and E2 have been included. When the alarm/exercise switch is in exercise mode and no minimum speed is set, the complimentary output of flip-flop F3 is high and therefore the output of andgate A2 is high. This enables exclusive-or-gates E1 and E2 to act as inverters. This inverts the output of the first two bits of memory latches L1/L2. Therefore comparator M1/M2 acts as if a "minimum speed" of three is stored in memory. This allows the present invention to pause the VCR when the bicycle stops or falls below the "minimum speed" of three. When an actual "minimum speed" is stored in memory by pressing the set-speed button, flip-flop F3 output is set to a high level. The complimentary output goes to a low level which inhibits A2. This causes E1 and E2 to simply pass the data in the first two bits of memory directly on to comparator M1/M2.

If instead of a bicycle providing clock pulses to RC1/RC2 an alarm clock or some other device provides the pulse, the present invention can act as an alarm. The alarm pulse will be seen by the circuit as a "present speed" of one. However, two additional functions are necessary. One is to eliminate E1 and E2 from the circuit so that the "minimum speed" of zero stored in memory can be accessed later. This is done by inhibiting A2 with the alarm/exercise switch set to an open position and the complimentary output of F3 which goes low once the alarm is triggered.

The second additional function is to allow the present invention to ignore any input data after the first input pulse is received by RC1/RC2. This allows the TV or VCR to stay off or paused once the alarm signal disappears which would be seen by the system as a "present speed" of zero. This is done with flip-flop F3. When the alarm/exercise switch is set to alarm or open position and the reset switch 118 is thrown, the complimentary output of F3 goes high and the output goes low. These outputs feed the cascade inputs of comparator M1/M2. When the complimentary output of F3 is high, M1/M2 thinks the "present speed" is loss than the "minimum speed" even though both are zero. It basically simulates the function of E1 and E2 when in exercise mode. When an input pulse clocks RC1/RC2, the present invention thinks the "present speed" is now greater than the "minimum speed" of zero and activates the remote control unit. However, once the input signal turns off, the system would once again think the "present speed" is less than the "minimum speed" and again activate the remote control unit. To prevent this, the output of A1 which activates the remote control unit also clocks F3 to a high output and low complimentary output. This allows M1/M2 to ignore previous comparator stages and recognize the actual "present speed" and "minimum speed" values. Since the "present speed" is always greater than or equal to the "minimum speed" of zero, any further input information is effectively ignored. An LED, D2, connected to the complimentary output of F3, lights when the present invention is ready to react to an alarm signal. Once the alarm is triggered, the LED turns off.

Several items should be noted. The analog components and timing elements of the circuit do not have critical values but should stay within certain limits for the present invention to operate effectively. See FIG. 6 for IC package numbers, FIG. 7 for the power supply circuit diagram, and FIG. 8 for the exterior sensor circuit diagram. The present invention uses a ripple counter instead of a synchronous counter because synchronous counters are much more sensitive to noise and voltage spikes. Ripple counters are more stable, easier to work with, and use half the power which is important for battery life. If synchronous counters would be used, circuit components P3 and A3 could be eliminated-since there would be no ripple delay to deal with. The exclusive-or gates, E1 and E2, which allow the present invention to control the VCR with no "minimum speed" set, also act as a damper to prevent circuit activation by a slow movement of the pedals. They are what preset the minimum speed, in effect, to three or four miles per hour. This is why two gates are used instead of one which would be all that is necessary to allow the present invention to operate the VCR when no minimum speed is set.

The present invention has several advantages over the previous art. The system contains no moving parts; therefore, no maintenance or periodic adjustment is needed.

It is simple to operate, especially for older or non-technical people. It can control a VCR, TV, or other common household device. It is Economical to produce and purchase. Its battery operation eliminates power cords. It has flexible input and output, since many types of exercise machines may be used. Its output can control many types of electronic devices. It provides effective motivational feedback to encourage continued exercising. Lastly, it has an alternate mode of operation as an alarm.

SUMMARY OF OPERATING STEPS

To Operate as an Exercise Aide:

1. Mount the external sensor assembly and metal tabs on the bicycle.

2. Plug phone jack into control box and set the EXERCISE/ALARM switch to EXERCISE.

3. Insert four C size batteries.

4. Program the remote control unit, using the enclosed manual, for the VCR and TV.

5. Press the "TV" button on the remote control unit. This will allow the TV "power" button to function as well as the VCR transport functions.

6. If a VCR is being used, load a tape in the VCR, play it, and pause it. If a TV is being used only, turn the TV off, otherwise leave it on.

7. Set the VCR/TV switch to the device to be controlled.

8. Throw the ON and RESET switches together. (The RESET switch will spring back).

9. Start pedaling the bicycle. When the speed reaches three or four miles per hour the VCR will start playing (or the TV will turn on).

10. To set a "minimum speed" in memory, press the SET-SPEED button when the desired speed is reached. The SPEED-SET LED will light when the button is pressed and go out when the speed has been stored in memory. 11. To change the "minimum speed" memory, press the SET-SPEED button again when the new speed is reached.

12. To reset the memory speed back to zero, stop the bicycle and throw the RESET switch. (Note: If the bicycle is not stopped, the VCR (or TV) may get out-of-sync with the bicycle since RESET clears all circuit memory elements. If this should happen, manually press the pause (or power) button on the remote control unit. also, if the SET-SPEED button is pressed while the bicycle is stopped, the "preset" speed of three or four miles per hour is set to zero. This means the bicycle has no control over the VCR (or TV) since the bicycle speed will always be equal to or greater than zero.

To Operate as an Alarm:

1. Set the VCR/TV switch to TV.

2. Set the EXERCISE/ALARM switch to ALARM.

3. Throw the ON and RESET switches together. (The RESET switch will spring back). Whenever the ALARM LED is not lit, the system is not "armed". Throw the RESET switch to arm the system. The present invention is now ready to react to a voltage pulse input. Once the alarm is triggered, the TV will turn off and the LED will go out.

A quick way to demonstrate the alarm function is to short the yellow and red wires of the external sensor cord momentarily. Another way is to start pedaling the bicycle. Either of these actions will send a voltage pulse to the present invention simulating a pulse from a smoke detector, door bell, oven timer or other device. The actual configuration of 5 volts, ground, and counter input wires used would depend on the external device sending the alarm signal.

Note: Discrete, single pulses are not necessary in alarm mode. The first pulse to reach the counter input triggers the present invention and any further signals are ignored.

Parts

Analog Components:

Resistors (ohms): R1—2.2K, R2—470K, R3—N0. 10K, R4—N0. 10K, R5—No. 10K, R6—330, R7—330

Capacitors (micro farads): C1—1, C2—0.01, C3—0.01, C4—0.001.

Spike Suppressors: 0.01 (6), 0.1 (1)

Timing Components:

T1—Master clock freq.: approx 1.5 Hz, Duty cycle approx. 50%

P1 & P2—Pulse width: approx. 40 micro sec.

P3—Pulse widths approx. 4 micro sec.

Note: Pulse widths are wider than necessary which provides a safety margin without impairing operation.

Power Supply Components:

Four C-size alkaline batteries 5.1 v Zener diode 10 ohm, 2 watt resistor

Current:

Circuit approx. 95 mA

External Sensor approx. 25 mA

Total approx. 120 mA

Est. running time: 59 hrs. or over one year of typical use of 20 minutes a day, three days a week.

External sensor:

Type: Infrared emitter and detector

Voltage limits: low level—0 to 0.8 volt; high level—2.1 to 5 volts

Negative going edge of voltage pulse clocks counter

Switches:

On/Off—SPST

Reset—SPDT, auto-flip

Set Speed Button—SPDT

VCR/TV—DPDT

Alarm/Exercise—DPDT

Light Emitting Diodes:

Speed-set and Alarm: 5 v, 2 mA

Remote Control Unit:

Radio Shacks®—ITZA®—programmable (any make will work) Power supply—3 v, unswitched Wiring leads:

Phone jack: Red—5 v out, Black—ground, Yellow—counter input, Green—unused

Circuit board:

Red w/tape—6 v

Black w/tape—ground

Red (long)—reset

Red (short)—Reg. 5 v to switches

Black (in middle)—from set-speed button

Black (by remote control)—to VCR/TV switch

Green (long, w/tape)—from external sensor

Green (in middle)—to speed-set LED Green (to left transistor)—from TV switch and to remote "power" button Green (to right transistor)—from VCR switch and to remote "pause" button Black w/dbl tape—from alarm switch Red w/dbl tape—to alarm LED As shown in FIGS. 11–14, an alternate embodiment includes a remote control housing 200 with a rectangular configuration having a top face, a bottom face, and a periphery integrally formed therebetween defining an interior space. The remote control housing has a plurality of television and VCR control buttons formed thereon as is conventional in the art. The housing has an arm 210 pivotally coupled at a first end thereof to a rear edge of the housing. As shown in FIG. 12, the arm of the remote control housing has a collapsed orientation wherein the arm abuts the housing and an erected orientation wherein the arm resides perpendicular with respect to the housing. By this structure, the remote control housing may be situated adjacent the legs of a user during exercise with the arm in the erected orientation thereof. It should be noted that such exercise may consist of the use of a exercise bicycle, stepper, or the like.

With reference now to FIG. 13, motion detection means 212 is provided. The motion detection means is coupled to a second end of the arm of the remote control housing. In use, the motion detection means generates an activation signal upon a leg of a user passing within a detection zone thereof. To afford additional versatility, the arm may be adapted to swivel in the erected orientation thereof. Ideally, the detection zone comprises an area constrained by a pair of planes which form an approximate 10 degree angle.

Figure 14:
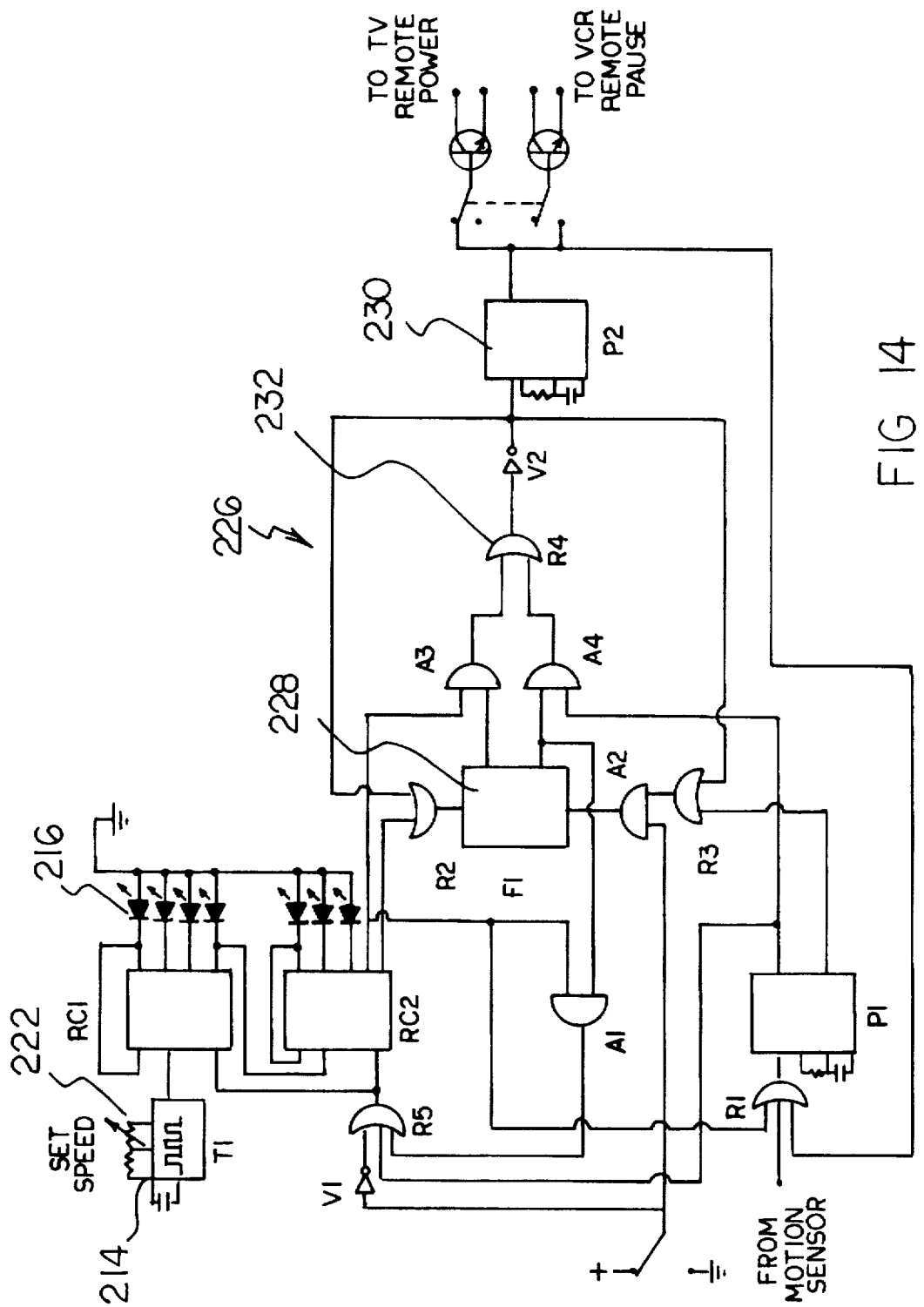
FIG. 14 is a detailed schematic diagram specifically depicting the electrical components of the alternate embodiment of the present invention.

Further provided as a component of the alternate embodiment is a counter means 214. Such counter means is situated within the remote control housing and electrically connected to the motion detection means. In operation, the counter means is adapted to transmit a deactivation signal upon the cessation of a predetermined time period. As shown in FIG. 14, the counter has a plurality of associated light emitting diodes 216 which are situated in linear alignment on the top face of the remote control housing. Such diodes are coupled to the counter means such that the number of diodes which are actuated is a function of the length of the predetermined time period. The control means ideally includes a free running 8 bit counter driven by pulse generator T1. See FIG. 14.

Also included is exercise speed control means 222 which is also situated within the remote control housing. The exercise speed control means is electrically connected to the counter means for allowing a user to selectively determine the predetermined time period. To facilitate the intended use of the speed control means, a speed control dial 224 is positioned on the top face of the remote control housing.

Control circuitry 226 is situated within the remote control housing and electrically connected to the counter means and the motion detection means. In use, the control circuitry is adapted to reset the counter means and further transmit a remote activation signal upon the receipt of the activation signal. The control circuitry is further adapted to reset the counter means and further transmit a remote deactivation signal upon the receipt of the deactivation signal. As shown in FIG. 14, the control circuitry relies on a flip flop 228, a pair of multivibrators 230, and a plurality of logic gates 232 for interconnecting the forgoing components of the present invention. By this design, the control circuitry is adapted to ensure that the activation signal and deactivation signal are not transmitted twice in a row. It should be noted that the signals which effect the resetting of the counter are always transmitted to ensure the proper operation thereof. The speed control dial of the speed control means may further be utilized for manually resetting the counter.

Also included is a remote control means 234 situated within the remote control housing and electrically connected to the control circuitry. Upon receiving the remote activation signal, the remote control means is adapted to generate a first infrared signal for activating the playback function of the videocassette recorder. When the remote deactivation signal is received, the remote control means generates a second infrared signal for activating the pause function of the videocassette recorder.

As in the previous embodiment, a videocassette recorder may be included for playing a videocassette in a playback function that is activated through receipt of a remote first infrared signal and a pause function that is activated through receipt of a remote second infrared signal. Optionally, the videocassette recorder may be excluded and a television may be adapted for activating upon the receipt of the remote first infrared signal and deactivating upon the receipt of the remote second infrared signal.

As an option, a function dial 238 may be positioned on a top face of the housing for allowing use o the present invention for various additional functions other than those previously described. For example, in an alarm mode, the remote control means may be adapted to actuate the television upon motion being detected. Also, in a sleep mode, the remote control means may be adapted to deactivate the television after a predetermined amount of time independent of motion.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and the manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modification and changes will readily occur to those skilled in the art, it is not desired to limit the invention to the exact construction and operation shown and described, and accordingly, all suitable modification and equivalents may be resorted to, falling within the scope of the invention.

What is claimed as being new and desired to be protected by Letters Patent of the United States is as follows:

1. A videocassette recorder remote controller mechanism comprising, in combination:

a remote control housing with a rectangular configuration having a top face, a bottom face, and a periphery integrally formed therebetween defining an interior space, the housing having an arm pivotally coupled at a first end thereof to a rear edge of the housing with a collapsed orientation wherein the arm abuts the housing and an erected orientation wherein the arm resides perpendicular with respect to the housing, whereby the remote control housing may be situated adjacent the legs of a user during exercise with the arm in the erected orientation thereof;

motion detection means coupled to a second end of the arm of the remote control housing for generating an activation signal upon a leg of a user passing within a detection zone thereof;

counter means situated within the remote control housing and electrically connected to the motion detection means, the counter means adapted to transmit a deactivation signal upon the cessation of a predetermined time period;

exercise speed control means situated within the remote control housing and electrically connected to the counter means for allowing a user to selectively determine the predetermined time period;

control circuitry situated within the remote control housing and electrically connected to the counter means and the motion detection means, the control circuitry adapted to reset the counter means and further transmit a remote activation signal upon the receipt of the activation signal, the control circuitry is further adapted to reset the counter means and further transmit a remote deactivation signal upon the receipt of the deactivation signal;

a videocassette recorder for playing a videocassette having a playback function that is activated through receipt of a remote first infrared signal and a pause function that is activated through receipt of a remote second infrared signal;

a television coupled to the videocassette recorder, the television being responsive to the videocassette recorder for displaying video that is electronically stored on videocassette to the user of the exercise bicycle when the playback function of the videocassette recorder is activated and pausing such video when the pause function of the videocassette recorder is activated; and remote control means situated within the remote control housing and electrically connected to the control circuitry adapted to generate a first infrared signal for activating the playback function of the videocassette recorder upon receiving the remote activation signal and for generating a second infrared signal for activating the pause function of the videocassette recorder when the remote deactivation signal is received.

2. A remote controller mechanism comprising:

motion detection means for generating an activation signal upon the detection of motion within a detection zone thereof;

counter means electrically connected to the motion detection means, the counter means adapted to transmit an deactivation signal upon the cessation of a predetermined time period;

control circuitry electrically connected to the counter means and the motion detection means, the control circuitry adapted to reset the counter means and further transmit a remote activation signal upon the receipt of the activation signal, the control circuitry is further adapted to reset the counter means and further transmit a remote deactivation signal upon the receipt of the deactivation signal; and remote control means electrically connected to the control circuitry adapted to generate a first infrared signal when the remote activation signal is received and for generating a second infrared signal when the remote deactivation signal is received.

3. A remote controller mechanism as set forth in claim 2 and further comprising a remote control housing with a rectangular configuration having a top face, a bottom face, and a periphery integrally formed therebetween defining an interior space, the housing having an arm pivotally coupled at a first end thereof to a rear edge of the housing with a collapsed orientation wherein the arm abuts the housing and an erected orientation wherein the arm resides perpendicular with respect to the housing, whereby the remote control housing may be situated adjacent the legs of a user during exercise with the arm in the erected orientation thereof, the motion detection means, counter means and control circuitry situated within the housing, the remote control means situated on a second end of the arm.

4. A remote controller mechanism as set forth in claim 2 and further comprising exercise speed control means electrically connected to the counter means for allowing a user to selectively determine the predetermined time period.

5. A remote controller mechanism as set forth in claim 2 and further including a videocassette recorder for playing a videocassette having a playback function that is activated through receipt of a remote first infrared signal and a pause function that is activated through receipt of a remote second infrared signal.

6. A remote controller mechanism as set forth in claim 2 and further including a television for activating upon the receipt of the remote first infrared signal and deactivating upon the receipt of the remote second infrared signal.

7. A remote controller mechanism comprising:

a remote control housing with a rectangular configuration having a top face, a bottom face, and a periphery integrally formed therebetween defining an interior space;

motion detection means situated on the remote control housing for generating a motion detection signal upon the detection of motion within a detection zone thereof;

control circuitry situated in the remote control housing and electrically connected to the motion detection means, the control circuitry adapted to transmit a remote activation signal in response to the receipt of the motion detection signal;

remote control means situated on the remote control housing and electrically connected to the control circuitry, the remote control means adapted to generate an infrared signal when the remote activation signal is received; and a television for activating from a deactivated mode upon the receipt of the infrared signal.

* * * * *